United States Patent
Kitamura et al.

(10) Patent No.: US 7,125,253 B2
(45) Date of Patent: Oct. 24, 2006

(54) DENTAL IMPLANT SYSTEM AND METHOD

(76) Inventors: Akira Kitamura, 36-26, Shiroyamadai 2-Chome, Nagasaki-shi, Nagasaki 852-8027 (JP); Ryoji Kitamura, 36-26, Shiroyamadai 2-Chome, Nagasaki-shi, Nagasaki 852-8027 (JP)

( * ) Notice: Subject to any disclaimer, the term of this patent is extended or adjusted under 35 U.S.C. 154(b) by 46 days.

(21) Appl. No.: 10/956,559

(22) Filed: Oct. 1, 2004

(65) Prior Publication Data
US 2005/0064368 A1    Mar. 24, 2005

Related U.S. Application Data

(63) Continuation-in-part of application No. PCT/JP03/03903, filed on Mar. 27, 2003.

(30) Foreign Application Priority Data
Apr. 4, 2002   (JP)   ............................. 2002-102295

(51) Int. Cl.
  *A61C 8/00*   (2006.01)
(52) U.S. Cl. ................. 433/173; 433/167; 433/215
(58) Field of Classification Search ............ 433/173, 433/172, 215, 167; 128/898
See application file for complete search history.

(56) References Cited

U.S. PATENT DOCUMENTS

| 4,682,951 | A | * | 7/1987 | Linkow | .................. 433/173 |
| 4,787,848 | A |   | 11/1988 | Ross | |
| 5,366,374 | A |   | 11/1994 | Vlassis | |
| 5,397,235 | A | * | 3/1995 | Elia | .......................... 433/173 |
| 5,456,601 | A | * | 10/1995 | Sendax | ...................... 433/173 |
| 5,885,079 | A | * | 3/1999 | Niznick | ..................... 433/174 |
| 5,989,025 | A | * | 11/1999 | Conley | ....................... 433/76 |
| 6,050,819 | A | * | 4/2000 | Robinson | .................. 433/173 |
| 6,537,070 | B1 | * | 3/2003 | Stucki-McCormick | ...... 433/174 |
| 2002/0102516 | A1 | * | 8/2002 | Srouji et al. | ............... 433/173 |
| 2002/0177102 | A1 | * | 11/2002 | Martin et al. | .............. 433/173 |

FOREIGN PATENT DOCUMENTS

| JP | S60-13114 | 1/1985 |
| JP | S62-39711 | 3/1987 |

OTHER PUBLICATIONS

Armand et al., "Radiographic and histologic evaluationof a sinus augmentation with composite bone graft: a clinical case report." *J. Periodontol.* 73(9):1082-1088, Sep. 2002 (abstract only).

(Continued)

Primary Examiner—Melba N. Bumgarner
Assistant Examiner—Jonathan Werner
(74) Attorney, Agent, or Firm—Alleman Hall McCoy Russell & Tuttle LLP

(57) ABSTRACT

A dental implant system and method are provided. The dental implant method may include forming a hole in bone of an alveolar of a maxilla, adjacent a sinus cavity. The hole is typically formed so as to leave a bridge portion separating the hole from a bottom surface of a sinus cavity wall. The method may further include separating the bridge portion from the sinus cavity wall, and lifting the bridge portion and the sinus membrane together at least partially into the sinus cavity.

21 Claims, 16 Drawing Sheets
(1 of 16 Drawing Sheet(s) Filed in Color)

OTHER PUBLICATIONS

Artzi et al., "Nonceramic hydroxyapatite bone derivative in sinus augmentation procedures: clinical and histomorphometric observations in 10 consecutive cases," *Int. J. Periodontics Restorative Dent.* 23(4):381-389, Aug. 2003 (abstract only).

Babbush, "Sinus lift revisited: an update on current implant-related procedures," *Dent. Implantol. Update* 9(1):1-5, Jan. 1998 (interview/abstract only).

Barber et al., "The status of implant training in oral and maxillofacial surgery residency programs," *J. Oral Maxillofac Surg.* 52(10):1058-1060, Oct. 1994 (abstract only).

Baumann and Ewers, "Minimally invasive sinus lift. Limits and possibilities in the atrophic maxilla," *Mund Kiefer Gesichtschir* 3 Suppl 1:S70-S73, May 1999 (abstract only).

Boyne et al., "Grafting of the maxillary sinus floor with autogenous marrow and bone," *J. Oral Surg.* 38:613-616, Aug. 1980.

Branemark et al., "An Experimental and Clinical Study of Osseointegrated Implants Penetrating the Nasal Cavity and Maxillary Sinus," *J. Oral Maxillofac Surg.* 42(8):497-505, Aug. 1984 (abstract only).

Buser and Tonetti, "Clinical trials on implants in regenerated bone," *Ann. Periodontol.* 2(1)329-342, Mar. 1997 (abstract only).

Cehreli and Sahin, "Biological Reactions to a Poly($_L$-lactide)-Hydroxyapatite Composite: A Study in Canine Mandible," *J. Biomaterials Applications* 17:265-276, Apr. 2003.

Chen, "Hydraulic sinus lift with sinus condensers. Interview." *Dent. Implantol. Update* 14(3):17-23, Mar. 2003 (interview/abstract only).

Coatoam, "Indirect sinus augmentation procedures using one-stage anatomically shaped root-form implants," *J. Oral Implantol.* 23(1-2):25-42, 1997 (abstract only).

Coatoam and Krieger, "A four-year study examining the results of indirect sinus augmentation procedures," *Oral Implantol.* 23(3):117-127, 1997 (abstract only).

Cordaro, "Bilateral simultaneous augmentation of the maxillarysinus floor with particulated mandible. Report of a technique and preliminary results," *Clin. Oral Implants Res.* 14(2):201-206, Apr. 2003 (abstract only).

Cosci and Luccioli, "A New Sinus Lift Technique in Conjunction With Placement of 265 Implants: A 6-Year Retrospective Study," *Implant Dent.* 9(4):363-368, 2000 (abstract only).

D'Amato et al., "Maxillary sinus surgical lift. Summers' technique versus lateral surgical approach," *Minerva Stomatol.* 49(7-8):369-381, Jul.-Aug. 2000 (abstract only).

Defrancq and Vanassche, "Less invasive sinus lift using the technique of Summers modified by Lazzara," *Rev. Belge Med. Dent.* 56(2):107-124, 2001 (abstract only).

Ellegaard et al., "Implant therapy involving maxillary sinus lift in periodontally compromised patients," *Clin. Oral Implants Res.* 8(4):305-315, Aug. 1997 (abstract only).

Engelke and Deckwer, "Endoscopically controlled sinus floor augmentation. A preliminary report," *Clin. Oral Implants Res.* 8(6):527-531, Dec. 1997 (abstract only).

Fugazzotto, "Sinus floor augmentation at the time of maxillary molar extraction technique and report of preliminary results," *Int. J. Oral Maxillofac Implants* 14(4):536-542, Jul.-Aug. 1999 (abstract only).

Gaggl et al., "Treatment planning for sinus lift augmentations through use of 3-dimensional milled models derived from computed tomography scans: a report of 3 cases," *Oral Surg. Oral Med. Oral Pathol. Oral Radiol. Endodi* 86(4):388-392, Oct. 1998 (abstract only).

Galli et al., "Chronic Sinusitis Complicating Sinus Lift Surgery," *Am. J. Rhinol.* 15(3):181-186, May-Jun. 2001.

Garg, "Augmentation grafting of the maxillary sinus for placement of dental implants: anatomy, physiology, and procedures," *Implant Dent.* 8(1):36-46, 1999 (abstract only).

Garg, "Nasal sinus lift: an innovative technique for implant insertions," *Dent. Implantol. Update* 8(7):49-53, Jul. 1997 (interview/abstract only).

Gray et al., "Assessment of the sinus lift operation by magnetic resonance imaging," *Br. J. Oral Maxillofac Surg.* 37(4):285-289, Aug. 1999 (abstract only).

Gray et al., "Magnetic resonance imaging assessment of a sinus lift operation using reoxidised cellulose (Surgicel) as graft material," *Clin. Oral Implants Res.* 12(5)526-530, Oct. 2001 (abstract only).

Haas et al., "A preliminary study of monocortical bone grafts for oroantral fistula closure," *Oral Surg. Oral Med. Oral Pathol. Oral Radiol. Endod.* 97(1):4, Jan. 2004 (abstract only).

Haas et al., "Bovine hydroxyapatite for maxillary sinus grafting: comparative histomorphometric findings in sheep," *Clin. Oral Implants Res.* 9(2):107-116, Apr. 1998 (abstract only).

Haas et al., "Five-year results of maxillary intramobile Zylinder implants," *Br. J. Oral Maxillofac Surg.* 36(2):123-128, Apr. 1998 (abstract only).

Haas et al., "Porous hydroxyapatite for grafting the maxillary sinus: a comparative histomorphometric study in sheep," *Int. J. Oral Maxillofac Implants* 17(3):337-346, May-Jun. 2002 (abstract only).

Heller and Heller, "Clinical evaluations of a porous-surfaced endosseous implant system," *J. Oral Implantol.* 22(3-4):240-246, 1996 (abstract only).

Jian et al., "Maxillary pre-implant rehabilitation: a study of 55 cases using autologous bone graft augmentation," *Rev. Stomatol. Chir. Maxillofac.* 100(5):214-220, Oct. 1999 (abstract only).

Johren et al., "Fear reduction in patients with dental treatment phobia," *Br. J. of Oral and Maxillofacial Surg.* 38:612-616, 2000.

Karabuda et al., "Histological and clinical evaluation of 3 different grafting materials for sinus lifting procedure based on 8 cases," *J. Periodontol.*72(10):1436-1442, Oct. 2001 (abstract only).

Kasabah et al., "Can we predict maxillary sinus mucosa perforation?" *Acta Medica (Hradec Kralove)* 46(1):19-23, 2003 (abstract only).

Kaufman, "Maxillary Sinus Elevation Surgery: An Overview," *J. Esthet. Restor. Dent.* 15(5):272-283, 2003.

Khoury, "Augmentation of the sinus floor with mandibular bone block and simultaneous implantation: a 6-year clinical investigation," *Int. J. Oral Maxillofac Implants* 14(4):557-564, Jul.-Aug. 1999 (abstract only).

Knabe and Hoffmeister, "The use of implant-supported ceramometal titanium prostheses following sinus lift and augmentation procedures: a clinical report," *Int. J. Oral Maxillofac Implants* 13(1):102-108, Jan.-Feb. 1998 (abstract only).

Krekmanov, "A modified method of simultaneous bone grafting and placement endosseous implants in the severely atrophic maxilla," *Int. J. Oral Maxillofac Implants* 10(6):682-688, Nov.-Dec. 1995 (abstract only).

Krekmanov and Heimdahl, "Bone Grafting to the maxillary sinus from the lateral side of the mandible," *British J. of Oral and Maxillofacial Surg.* 38:617-619, 2000.

Lambrecht, "Intraoral piezo-surgery," *Schweiz Monatsschr Zahnmed.* 114(1):28-36, 2004 (abstract only).

Landi et al., "Maxillary sinus floor elevation using a combination of DFDBA and bovine-derived porous hydroxyapatite: a preliminary histologic and histomorphometric report," *Int. J. Periodontics Restorative Dent.* 20(6):574-583, Dec. 2000 (abstract only).

Laster et al., "A new tricortical implant," *Refuat Hapeh Vehashinayim.* 20(3):89-95, 105, Jul. 2003 (abstract only).

Lazzara et al., "The sinus elevation procedure in endosseous implant therapy," *Curr. Opin. Periodontol.* 3:178-183, 1996 (abstract only).

Leder et al., "Reconstruction of the severely atrophic maxilla with autogenous bone graft and hydroxylapatite/decalcified freeze-dried bone allograft in the same patient: a preliminary report," *Periodontal Clin. Investig.* 15(1):5-9, Fall 1993 (abstract only).

Lekholm, "New surgical procedures of the osseointegration technique A.M. Branemark," *Aust. Prosthodont J.* 7 Suppl:25-32, 1993 (abstract only).

Levin et al., "Smoking and complications of onlay bone grafts and sinus lift operations," *Int. J. Oral Maxillofac Implants* 19(3):369-373, May-Jun. 2004 (abstract only).

Lim et al., "Intentional Angulation of an Implant to Avoid a Pneumatized Maxillary Sinus: A Case Report," *J. Canadian Dental Assoc.* 70(3):164-168, Mar. 2004.

Marx and Garg, "A novel aid to elevation of the sinus membrane for the sinus lift procedure," *Implant Dent.* 11(3):268-271, 2002 (abstract only).

Mazor et al., "Sinus augmentation for single-tooth replacement in the posterior maxilla: a 3-year follow-up clinical report," *Int. J. Oral Maxillofac Implants* 14(1):55-60, Jan.-Feb. 1999 (abstract only).

Mazor et al., "The use of hydroxyapatite bone cement for sinus floor augmentation with simultaneous implant placement in the atrophic maxilla. A report of 10 cases." *J Periodontol.* 71(7):1187-94, Jul. 2000 (abstract only).

Murakami et al., "Periodontal and computer tomography scanning evaluation of endosseous implants in conjunction with sinus lift procedure. A case series," *J. Periodontol.* 70(10):1254-1259, Oct. 1999 (abstract only).

Muronoi et al, "Simplified procedure for augmentation of the sinus floor using a haemostatic nasal balloon," *Br. J. Oral Maxillofac Surg.* 41(2):120-121, Apr. 2003 (abstract only).

Nedir et al., "A 7-year life table analysis from a prospective study on ITI implants with special emphasis on the use of short implants. Results from a private practice." *Clin. Oral Implants Res.* 15(2):150-157, Apr. 2004 (abstract only).

Nocini et al., "Implant placement in the maxillary tuberosity: the Summers' technique performed with modified osteotomes" *Clin. Oral Impl. Res.* 11:273-278, 2000.

Olson et al., "Long-term assessment (5 to 71 months) of endosseous dental implants placed in the augmented maxillary sinus," *Ann Periodontol.* 5(1):152-156, Dec. 2000 (abstract only).

Pacifici et al., "Lifting of the maxillary sinus: complementary use of platelet rich plasma, autologous bone deproteinised bovine bone. Case report," *Minerva Stomatol* 52(9):471-478, Sep. 2003 (abstract only).

Partridge and Hostalet, "New harvesting technique for bone grafting. Case reports." *J. Indiana Dent. Assoc.* 82(2):19-22, Summer 2003 (abstract only).

Peleg et al., "Radiological findings of the post-sinus lift maxillary sinus: a computerized tomography follow-up," *J. Periodontol.* 70(12):1564-1573, Dec. 1999 (abstract only).

Quinones et al., "Maxillary sinus augmentation using different grafting materials and dental implants in monkeys. Part IV. Evaluation of hydroxyapatite-coated implants," *Clin. Oral Implants Res.* 8(6):497-505, Dec. 1997 (abstract only).

Rosen et al., "The bone-added osteotome sinus floor elevation technique: multicenter retrospective report of consecutively treated patients," *Int. J. Oral Maxillofac Implants* 14(6):853-858, Nov.-Dec. 1999 (abstract only).

Rosenlicht and Tarnow, "Human histologic evidence of integration of functionally loaded hydroxyapatite-coated implants placed simultaneously with sinus augmentation: a case report 2 ½ years postplacement," *J. Oral Implantol.* 25(1):7-10, 1999 (abstract only).

Sader et al., "Significance of profile prognosis in implant management of the atrophic maxilla," *Mund Kiefer Gesichtschir* 3 Suppl 1:S48-S52, May 1999 (abstract only).

Scher, "Use of the incisive canal as a recipient site for root form implant: preliminary clinical reports," *Implant Dent.* 3(1):38-41, Spring 1994 (abstract only).

Shiota et al., "Clinical retrospective study on outpatients at clinic for oral implants," *Kokubyo Gakkai Zasshi* 66(1):15-19, Mar. 1999 (abstract only).

Smiler et al., "Sinus lift grafts and endosseous implants. Treatment of the atrophic posterior maxilla," *Dent. Clin. North Am.* 36(1):151-186, Jan. 1992.

Soltan and Smiler, "Trephine bone core sinus elevation graft," *Implant Dent.* 13(2):148-152, Jun. 2004 (abstract only).

Strietzel et al., "Peri-implant alveolar bone loss with respect to bone quality after use of the osteotome technique: results of a retrospective study." *Clin. Oral Implants Res.* 13(5):508-513, Oct. 2002 (abstract only).

Sulzer et al., "Indications for oral implantology in a referral clinic. A three-year retrospective analysis of 737 patients with 1176 implants," *Schweiz Monatsschr Zahnmed.* 114(5):444-450, 2004 (abstract only).

Summers, "Sinus Floor Elevation with Osteotomes," *J. Esthet. Dent.* 10(3):164-171, 1998 (abstract only).

Szabo, "Use of biomaterials for preventive and restorative purposes," *Fogorv Sz.* 85(3):65-69, Mar. 1992 (abstract only).

Tepper et al., "Effects of sinus lifting on voice quality," *Clin. Oral Impl. Res.* 14:767-774, 2003.

Thunthy et al., "An illustrative study of the role of tomograms for the placement of dental implants," *J. Oral Implantol.* 29(2):91-95, 2003 (abstract only).

Timmenga et al., "Maxillary sinus function after sinus lifts for the insertion of dental implants," *J. Oral Maxillofac Surg.* 55(9):936-939; discussion 940, Sep. 1997 (abstract only).

Tong et al., "A review of survival rates for implants placed in grafted maxilla sinuses using meta-analysis," *Int. J. Oral Maxillofac Implants* 13(2):175-182, Mar.-Apr. 1998 (abstract only).

Vachiramon et al., "Delayed immediate single-step maxillary sinus lift using autologous fibrin adhesive in less than 4-millimeter residual alveolar bone: a case report," *J. Oral Implantol.* 28(4):189-193, 2002 (abstract only).

Valentini and Abensur, "Maxillary sinus grafting with anorganic bovine bone: a clinical report of long-term results," *Int. J. Oral Maxillofac Implants* 18(4):556-560, Jul.-Aug. 2003.

van den Bergh et al., "Anatomical aspects of sinus floor elevations," *Clin. Oral Implants Res.* 11(3):256-265, Jun. 2000 (abstract only).

Vassos and Petrik, "The sinus lift procedure: an alternative to the maxillary subperiosteal implant," *Pract. Periodontics Aesthet. Dent.* 4(9):14-19, Nov.-Dec. 1992 (abstract only).

Weingart and Ten Bruggenkate, "Treatment of fully edentulous patients with ITI implants," *Clin. Oral Implants Res.* 11 Suppl 1:69-82, 2000 (abstract only).

Wheeler et al., "Six-year clinical and histologic study of sinus-lift grafts," *Int. J. Oral Maxillofac Implants* 11(1):26-34, Jan.-Feb. 1996 (abstract only).

Woo and Le, "Maxillary Sinus Floor Elevation: Review of Anatomy and Two Techniques," *Implant Dentistry* 13(1):28-32, 2004.

Xu et al., "Experimental sinus grafting with the use of deproteinized bone particles of different sizes," *Clin. Oral Implants Res.* 14(5):548-555, Oct. 2003 (abstract only).

Zhao et al., "Maxillary sinus lifting and simultaneously placement of implants from the top of alveoli," *Zhonghua Kou Qiang Yi Xue Za Zhi* 38(4):251-253, Jul. 2003 (abstract only).

Zide, "Autogenous bone harvest and bone compacting for dental implants," *Compend. Contin. Educ. Dent.* 21(7):585-590; quiz 592, Jul. 2000 (abstract only).

Zinner et al., "Provisional and definitive prostheses following sinus lift and augmentation procedures," *Implant Dent.* 3(1):24-28, Spring 1994 (abstract only).

Zinner and Small, "Sinus-lift graft: using the maxillary sinuses to support implants," *J. Am. Dent. Assoc.* 127(1):51-57, Jan. 1996 (abstract only).

\* cited by examiner

DENTAL IMPLANT SYSTEM AND METHOD

CROSS-REFERENCE TO RELATED APPLICATIONS

This application is a continuation-in-part of PCT International Application No. PCT JP03/03903, now published as WO 03/084426, filed Mar. 27, 2003, entitled DRILL DEVICE FOR IMPLANTING, which in turn claims priority to Japanese Patent Application No. 2002-102295, filed Apr. 4, 2002. The entire disclosure of each of these applications is herein incorporated by reference for all purposes.

TECHNICAL FIELD

The present invention generally relates to an implant system including a plurality of dental devices and an implant method for using same to install a dental implant in an alveolar bone of a maxilla of a patient.

BACKGROUND

One type of dental implant typically is cylindrical in shape with an outer diameter of between about 4 and 5 millimeters, and is inserted to a fixed depth into the alveolar bone of the maxilla (upper jaw). For patients with an alveolar bone thickness of more than about 5 millimeters, this type of implant may be secured in a relatively stable manner. However, for patients with less than 5 millimeter alveolar bone thickness, dental surgeons use a procedure known as sinus lift bone augmentation to build up the thickness of the alveolar bone of the maxilla, so that dental implants may be securely installed therein.

As shown in FIG. 1, prior sinus lift bone augmentation procedure requires that the side wall bone of the maxillary sinus cavity be broken and a hole opened therein. The sinus cavity membrane is separated from the upper surface of the maxilla, and an elevator material made of a mixture of bone material and blood serum is inserted through the hole in the side of the maxilla and placed at the bottom of the sinus cavity between the maxilla and the sinus lining. The elevator material hardens over time to increase the effective thickness of the maxilla, thereby providing additional stability for the implant.

While this prior sinus lift bone augmentation procedure may be effective when performed by highly skilled surgeons, it nonetheless involves several inherent risks. First, exposure of the bone when the side wall of the sinus cavity is broken creates the risk of infection. Second, breaking the bone in the side wall or bottom of the sinus cavity creates a risk of penetration of the membrane lining the sinus cavity, which can further result in infection. Finally, during installation of the elevator material and implant itself, it is difficult to judge the amount of elevator material and depth of implant penetration into the sinus cavity, creating a risk that insufficient filler has been added, which, could weaken the implant, or a risk of overpenetration by the elevator material or implant, which could damage the sinus membrane. If the sinus membrane is ruptured, the transplanted elevator material may become infected. Further, this complicated procedure may involve hospitalization of the patient, which is time consuming and expensive.

It is also known to punch through from a tooth socket into the maxillary sinus cavity using a circular instrument as illustrated in FIG. 2. The instrument is then removed to form a hole in which an implant may be fastened. However, when using this procedure, it is difficult to determine whether the lower portion of the maxillary sinus cavity can be safely lifted up without fracture of the alveolar bone and the bottom of the sinus cavity wall. Therefore, success of this procedure is greatly dependent upon the skill of the dental surgeon performing the operation.

SUMMARY

A dental implant system and method are provided. The dental implant method typically includes forming a hole in bone of an alveolar of a maxilla, adjacent a sinus cavity. The hole is initially formed so as to leave a bridge portion separating the hole from a bottom surface of a sinus cavity wall. The method may further include freeing the bridge portion from the sinus cavity wall, and lifting the bridge portion and the sinus membrane together at least partially into the sinus cavity.

According to another aspect of the invention, the method may further include separating the sinus membrane from the sinus cavity wall, to thereby create a void, and further lifting the freed bridge portion into the sinus cavity to enlarge the void. The method may further include placing elevator material into the void, and inserting an implant into the hole, such that an inward end of the implant extends into the void and is surrounded by elevator material.

The dental implant system typically includes a scoring device having a shaft sized to be inserted into a predrilled hole in the alveolar bone. A bridge portion is formed in the alveolar bone at an end of the hole which separates the hole from the maxillary sinus cavity. The scoring device typically further includes a scoring edge positioned adjacent a distal end of the shaft, the scoring edge being configured to form a circular score in a portion of the alveolar bone when the shaft is rotated and pressed into the alveolar bone. The scoring device typically further includes a cavity formed inside of the scoring edge, the cavity being sized to accommodate bone material as the scoring edge penetrates the alveolar bone.

The implant system may further include a first lifting device having a shaft sized to be inserted into the hole. The first lifting device further typically includes a lifting portion positioned adjacent a distal end of the shaft, the lifting portion being sized to contact the bridge portion inward of the score, such that when upward pressure is applied to the lifting portion, the lifting portion is configured to break the alveolar bone along the score to free the bridge portion.

The implant system may further include a membrane separation elevator having a separation elevator shaft, and a separation elevator head that is substantially flat and attached at a distal end of the shaft. The separation elevator shaft is configured to be inserted through the neck in the hole, into the sinus cavity. The separation elevator head is configured to inserted between a sinus membrane and the sinus cavity wall, to cause separation therebetween.

The implant system may further include a second lifting device having a second lifting device shaft sized to be inserted into the hole, and a second lifting device end portion positioned adjacent a distal end of the shaft. The second lifting device end portion is typically longer than the first lifting device end portion and has a diameter that is sized to fit into the neck of the hole. The second lifting device end portion is configured to contact the freed bridge portion to further raise the freed bridge portion and sinus membrane together to a second predetermined penetration distance into the sinus cavity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
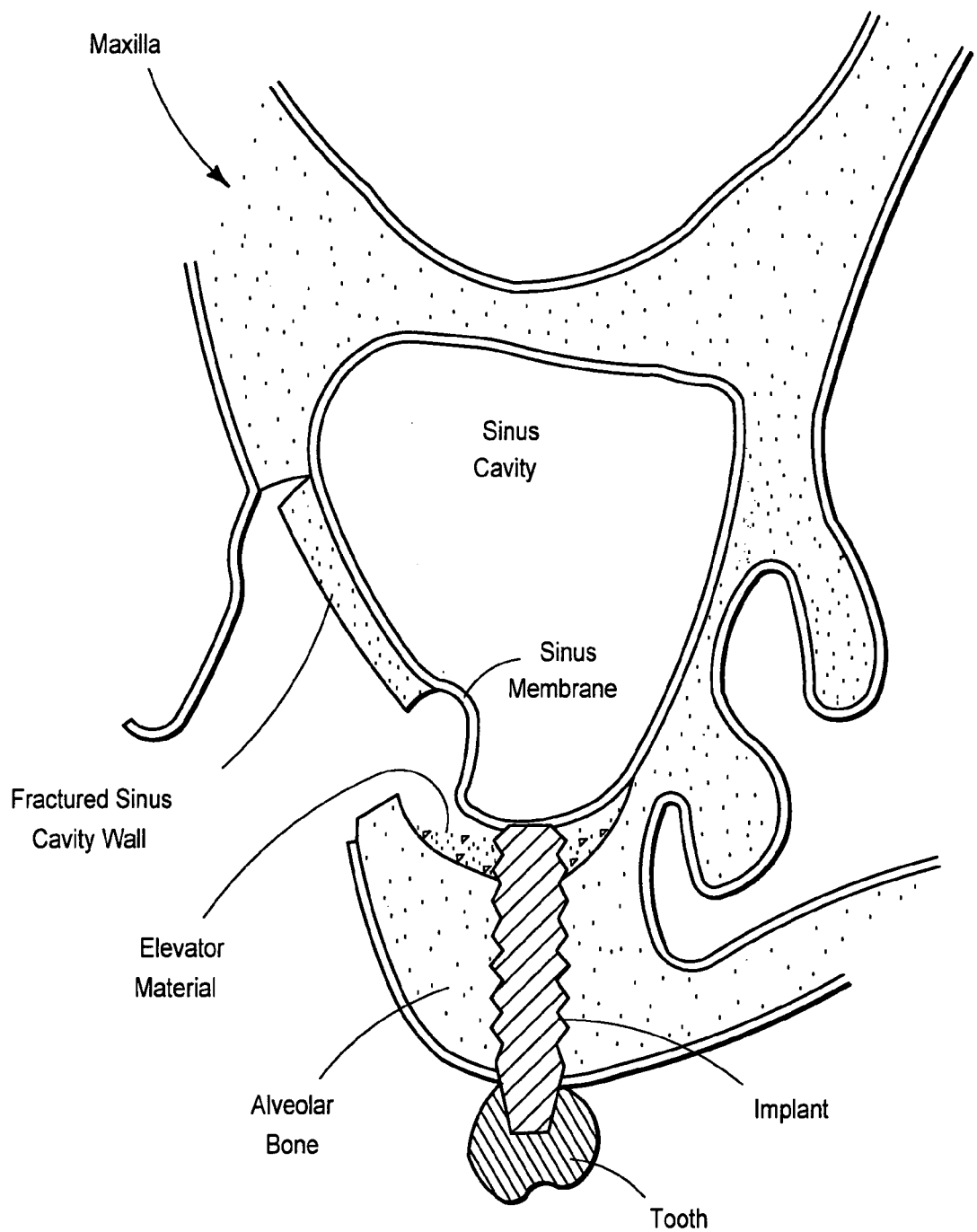
FIG. 1 is a cross-sectional view of a dental implant installed according to a prior art sinus lift bone augmentation procedure.
Figure 2:
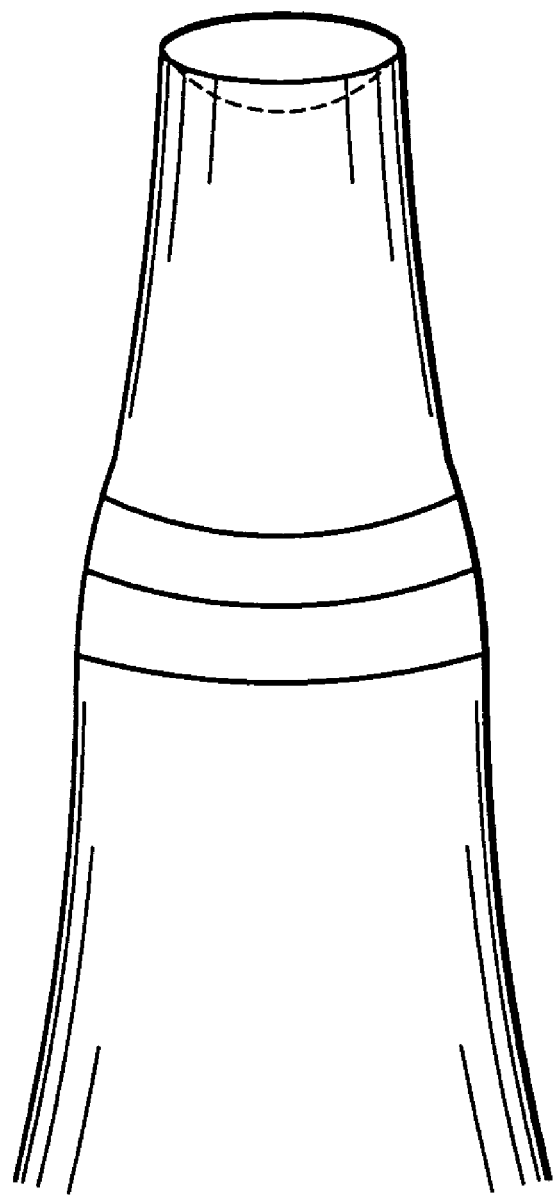
FIG. 2 is frontal view a prior art circular instrument for punching a hole in an alveolar bone to install a dental implant.
Figure 3:
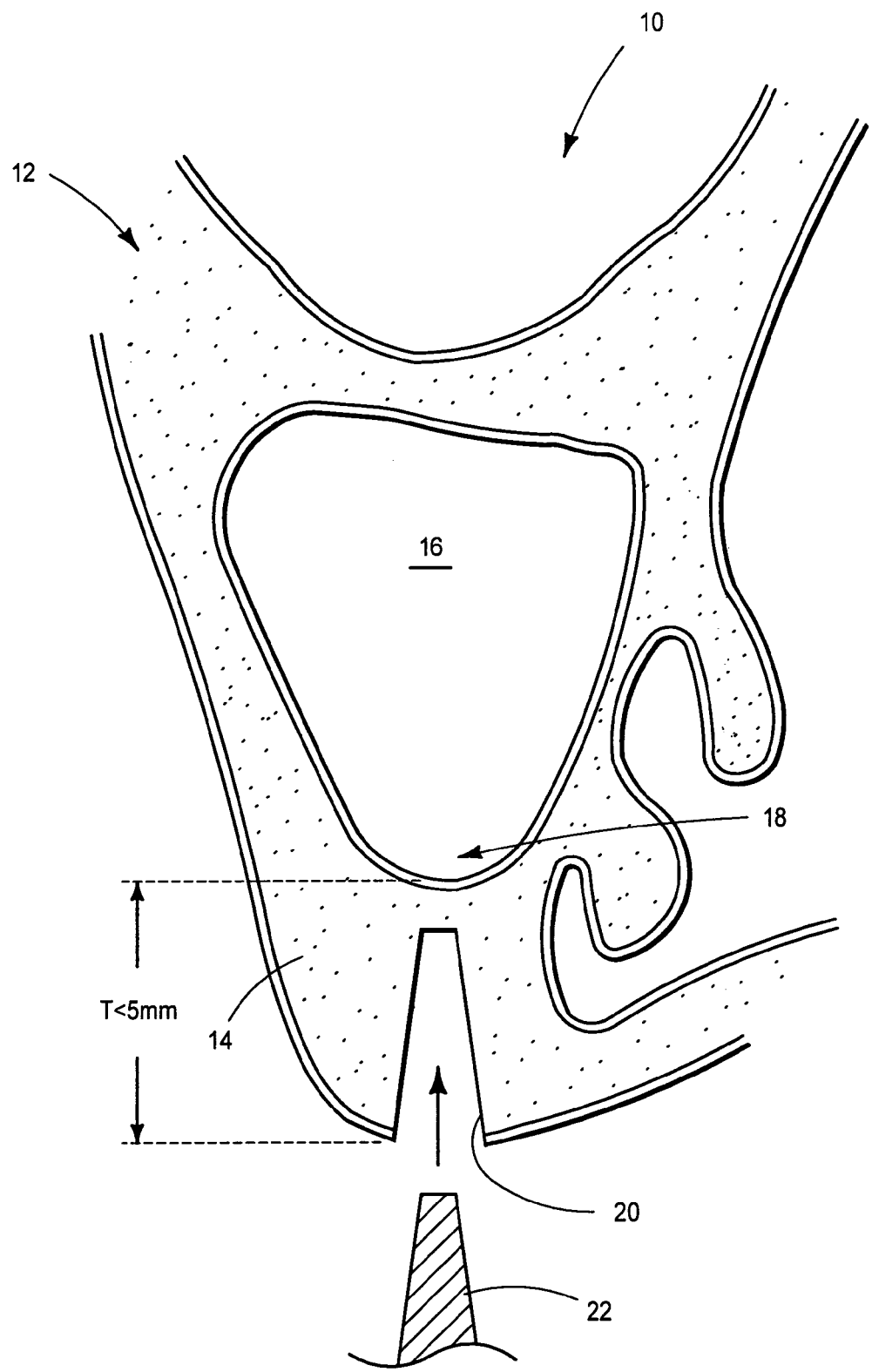
FIG. 3 is a cross-sectional view of an alveolar bone and maxillary sinus cavity, illustrating a predrill device used to predrill a hole according to one embodiment of a method for implanting a dental implant according to the present invention.

FIGS. 3–9 illustrate a method of implanting a dental implant, according to one embodiment of the present invention. FIG. 3 illustrates a cross section of a patient upper jaw region 10, showing a maxilla 12 having an alveolar bone 14 with a thickness T of less than about 5 millimeters (drawing not to scale) between the bottom of a sinus cavity 16 and a lower surface of the alveolar bone 14. This thickness is typically insufficient to properly support a dental implant, and therefore a sinus lift bone augmentation method according to the present invention may be used to add bone material in a lower region 18 of the sinus cavity 16 to provide additional support to the implant.

The implant method typically includes predrilling a hole 20 in alveolar bone 14 of the maxillary 12 with a predrill device 22. Typically, predrill device 22 is a tapered drill with a base diameter of approximately 3 millimeters. Alternatively, drills of other suitable sizes and shapes may be used. The predrill hole is formed to stop short of sinus cavity 16, and is formed with tapered sides, in a frustoconical shape.

Figure 4:
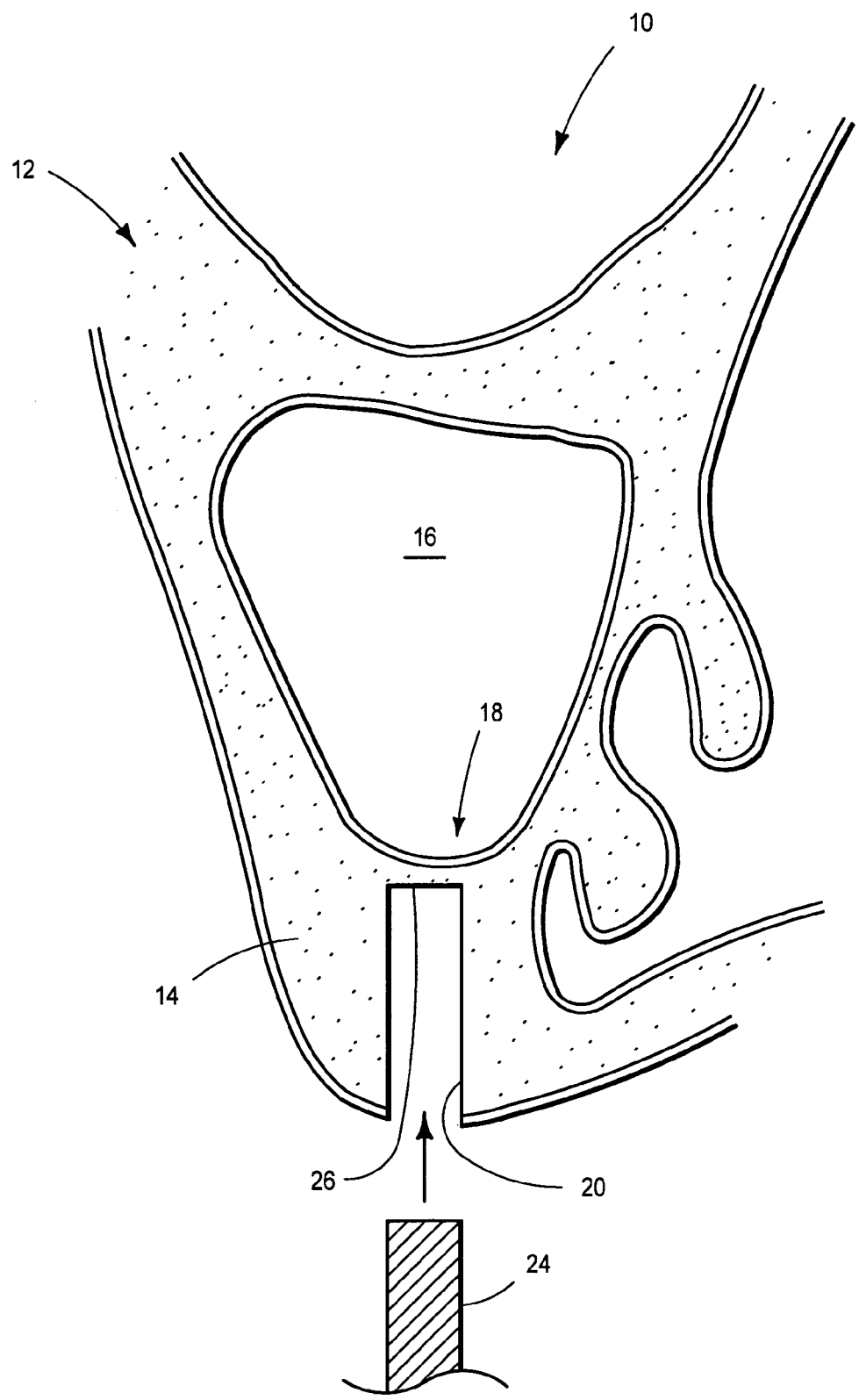
FIG. 4 is a cross-sectional view of an alveolar bone and maxillary sinus cavity, illustrating a boring device used in boring a hole in the alveolar bone.

As shown in FIG. 4, the implant method further typically includes boring a hole using a boring device 24 to remove the taper formed by the predrill device, and to leave a narrow bridge portion 26 remaining between the hole 20 and a lower region 18 of the sinus cavity 16. Typically, the bridge portion 26 is formed to a thickness of between 0.5 and 2 millimeters, and more typically to about 1 millimeter. The thickness of the bridge portion is ascertained by referencing tomography images of the patient jaw structure, and by visually monitoring a depth gauge formed by markings or grooves (see 70–76 in FIG. 10 or 130 in FIG. 13) on the boring device 24 as the device is inserted and twisted to deepen and bore out hole 20. It will be appreciated that the various other devices described herein are similarly marked to provide a depth gauge. Boring device 26 is typically connected to a handle, and is rotated by hand at low speed to prevent the generation of heat that might damage the bone.

Figure 5:
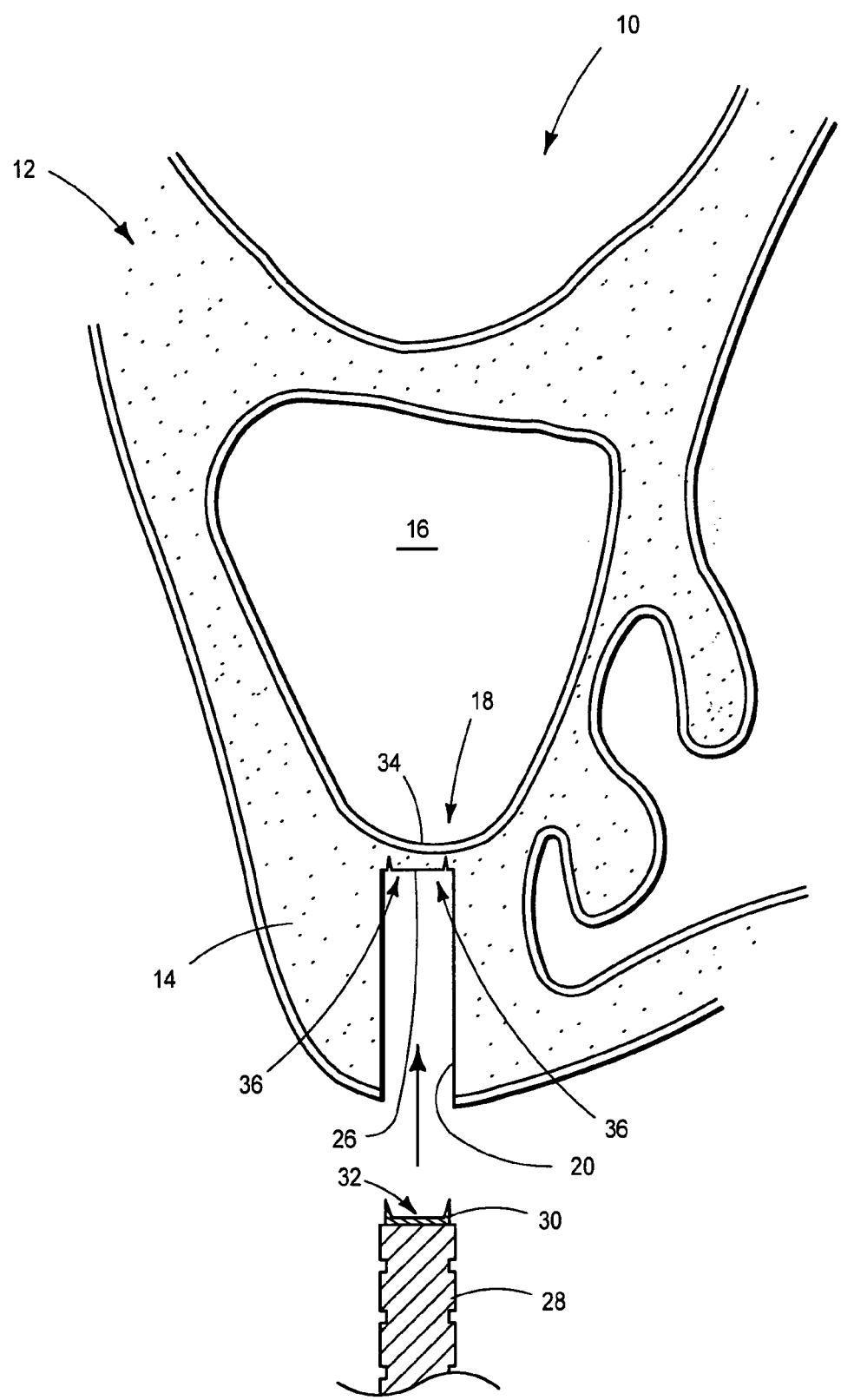
FIG. 5 is a cross-sectional view of an alveolar bone and maxillary sinus cavity, illustrating a scoring device used in scoring a bridge portion formed in the alveolar bone.

As shown in FIG. 5, the method typically includes scoring a bottom side of the bridge portion 26 with a scoring device 28. The scoring device is typically rotated by hand. The scoring device includes a scoring structure 30 configured to score the alveolar bone at the top end of hole 20. Typically, the scoring structure is a sharp, raised scoring edge formed in a circle around a circumference of a top portion of the scoring device. Alternatively, a blade that does not extend around the entire circumference may be used. A concavity 32 is formed within the scoring structure, to accommodate bone material as the scoring device is pressed into the bone surface. The cavity of the scoring device includes a floor configured to contact a portion of the alveolar bone to thereby stop penetration of the scoring edge into the alveolar bone at a predetermined penetration distance. The score 36 typically extends substantially all of the way through bridge portion 26, but does not extend all of the way through.

The scoring device is twisted by hand and forced into the bone by applying pressure sufficient to score the bone. Care is taken not to rotate bridge portion 26 relative to sinus membrane 34, which could damage the sinus membrane 34 and potentially cause infection. A narrow score 36, or indentation 36, is formed by rotation of the scoring device into bridge portion 26. Typically the scoring tool includes a lip or edge, as shown at 81 in FIG. 11 and 136 in FIG. 14, and the scoring edge is configured to form the circular score 26 inward of the edges of hole 20, such that the score 26 has a diameter that is less than the outside diameter of hole 20.

Figure 6:
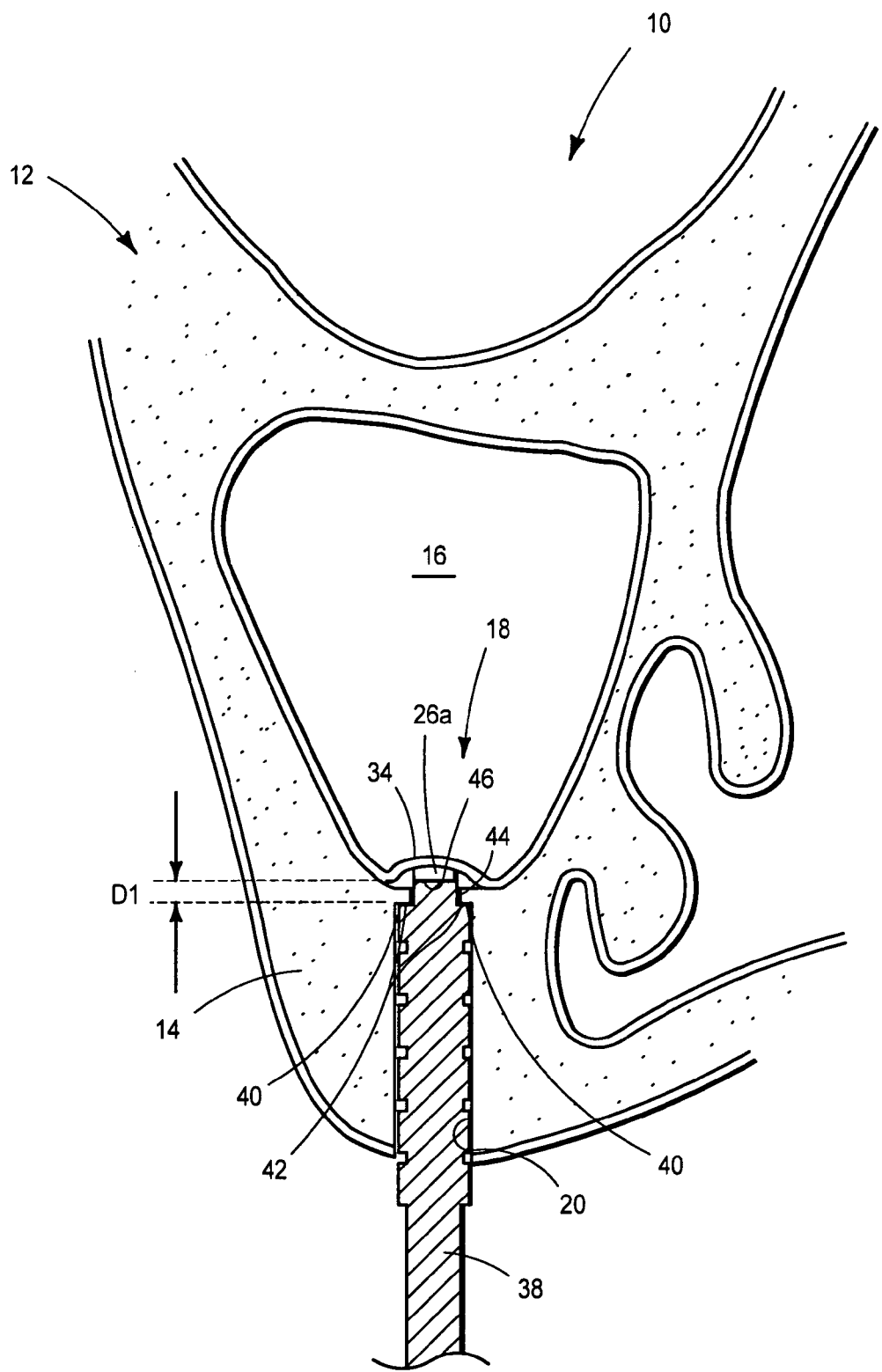
FIG. 6 is a cross-sectional view of an alveolar bone and maxillary sinus cavity, illustrating a first lifting device used in lifting a bridge portion and sinus membrane at least partially into the maxillary sinus cavity.

As shown in FIG. 6, the method includes lifting a portion of the sinus membrane 34 in tandem with the bridge portion 26, by inserting a first lifting device 38 into hole 20 and applying upward pressure. The bone breaks along the score 36 to thereby free the bridge portion, and create a freed bridge portion 26a. Because score 36 is formed inward of the sides of hole 20, as the freed bridge portion is raised, overhang portions 40 are formed along the sides of the hole, creating a narrowed neck at the upper end of the hole between the overhang portion 40. Typically, care is taken not to rotate the first lifting device 38 during the lifting operation, which could cause the bridge portion to rotate relative to the membrane. This prevents undesirable shear or tearing of the membrane.

The first lifting device is typically pushed upward a first predetermined lift distance D1 into the sinus cavity. Typically, the first lifting device includes a lip 42 configured to contact the overhang portions 40 of hole 20, when the freed bridge portion 26a reaches the first predetermined lift distance D1. A lifting portion 44 of the first lifting device 38 is formed such that a top surface 46 of the lifting portion supports the bridge portion 26a at the first predetermined lift distance D1 when the overhang portions 40 contact lip 42. This contact prevents further ingress of the first lifting device 38. In addition, markings that function as a depth gauge are provided on the shaft (see 152 in FIG. 15A and 102–108 in 12A), which may be visually monitored by the dental surgeon performing the operation to judge lift distance. It will be appreciated that according to another embodiment of the invention, overhang portions 40 may be omitted, and the dental surgeon performing the procedure may relay only on markings or grooves along the devices themselves to determine penetration distance, rather than on contact between a lip of a tool and an overhang portion of hole 20.

The predetermined lift distance D1 is a distance effective to allow the membrane separating device access to the sinus cavity, but not so far as to cause damage to sinus membrane 34. The first predetermined lift distance D1 typically is between 0.5 and 1.5 millimeters, and more typically is 1 millimeter, although variations are possible.

Figure 7:
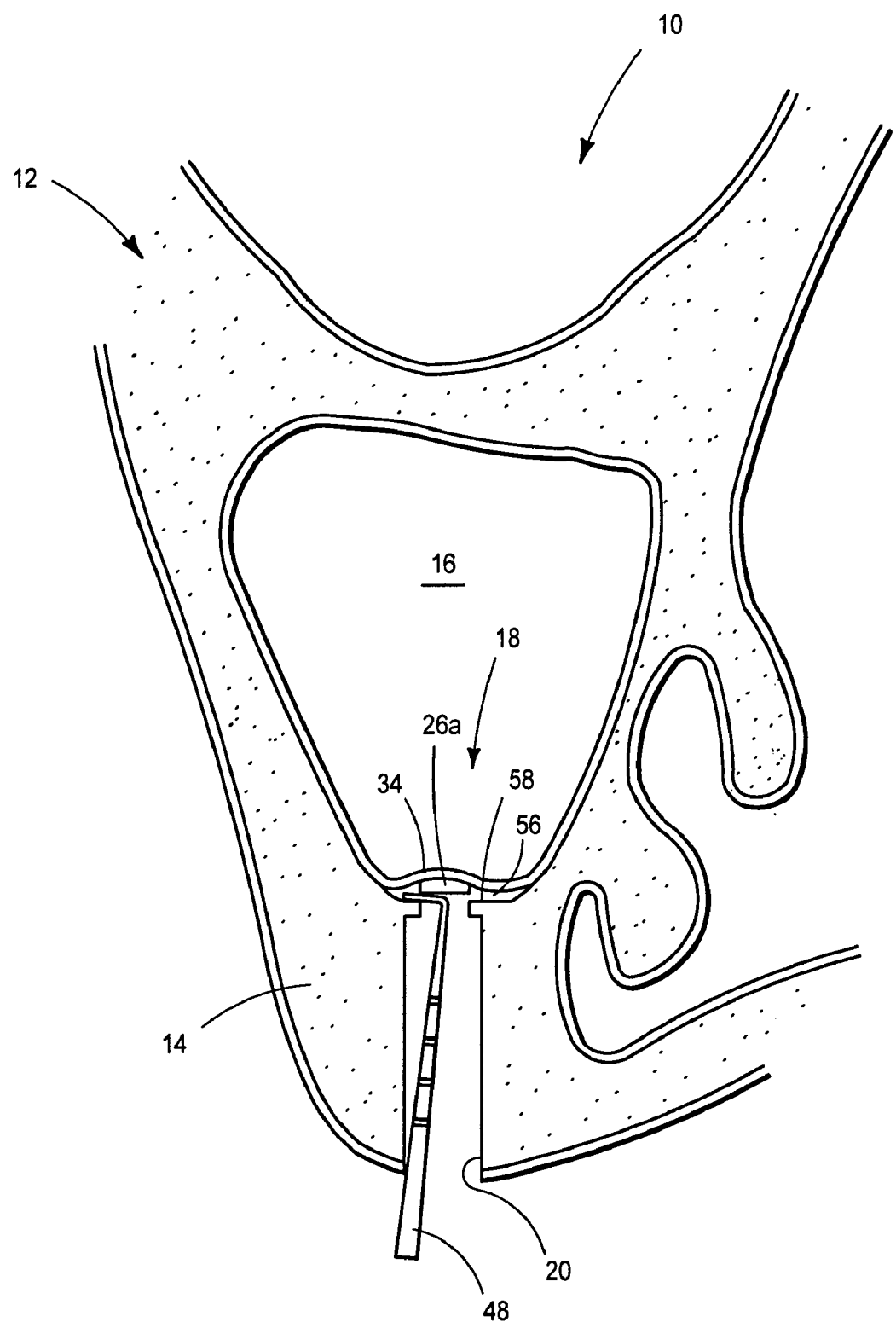
FIG. 7 is a cross-sectional view of an alveolar bone and maxillary sinus cavity, illustrating a membrane separating device used to separate the sinus membrane from a sinus cavity wall.
Figure 16A:
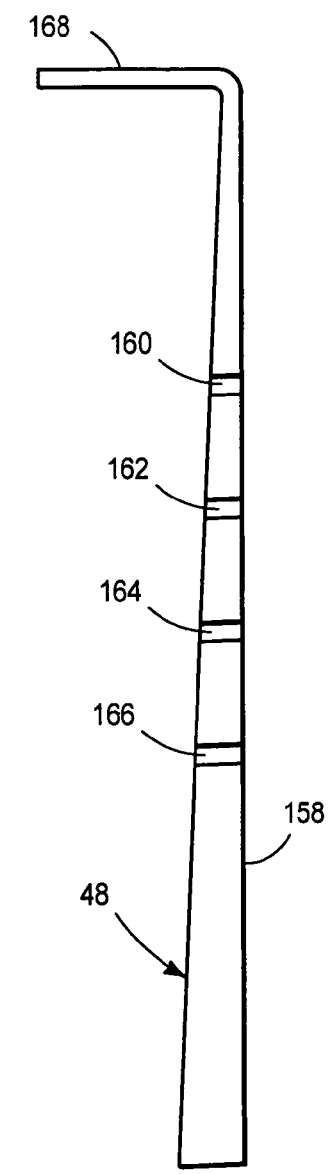
FIG. 16 is a front perspective view of a membrane separation elevator according to an embodiment of the present invention.
Figure 16B:
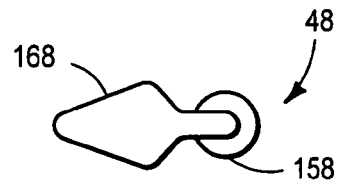

As shown in FIG. 7, the method includes separating the sinus membrane 34 from a sinus cavity wall 58 using a membrane separation elevator 48. As shown in FIG. 16B, membrane separation elevator 48 typically includes a flat, substantially triangular head 168. Head 168 is inserted between the sinus membrane 34 and the sinus cavity wall 58, and is rotated around the circumference of the upper opening of hole 20, to separate the membrane from the sinus cavity wall 58. As shown in FIG. 16A, membrane separation elevator 48 also typically includes grooves or markings 162–166, which form a depth gauge that indicates a penetration depth into the hole 20.

Figure 8:
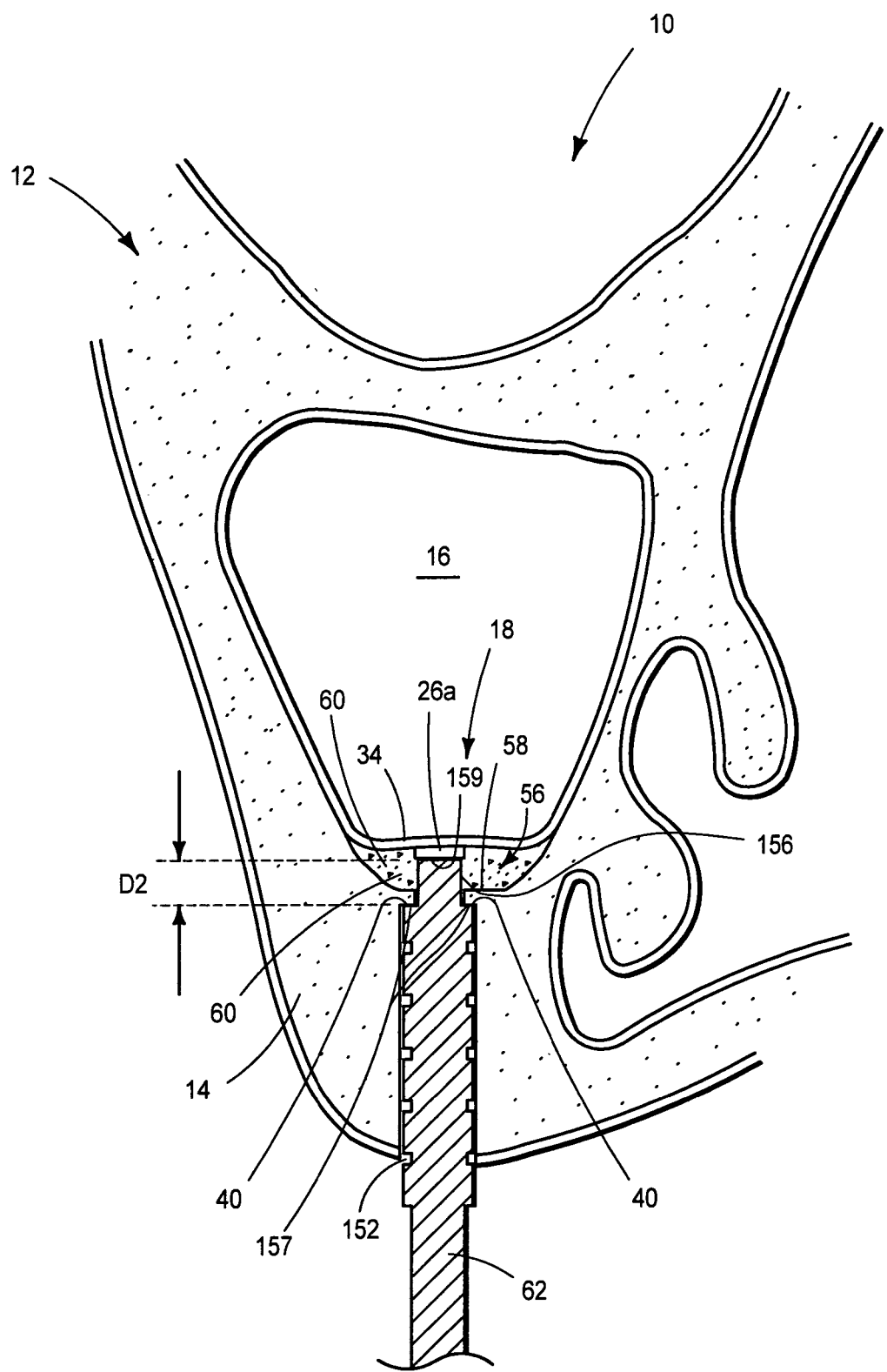
FIG. 8 is a cross-sectional view of an alveolar bone and maxillary sinus cavity, illustrating a second lifting device used to further lift a bridge portion and sinus membrane into the maxillary sinus cavity.

As shown in FIG. 8, the method may further include lifting the freed bridge portion 26a a second predetermined lift distance D2, using a second lifting device 62 having a lifting portion 156 with an effective length (length from top surface 159 to lip 157) that is greater than the first lifting device 38. Typically, the dental surgeon performing the implant method references grooves 152 or markings to judge penetration depth into hole 20. In the act of lifting the freed bridge portion 26a to the second predetermined lift distance D2, the sinus membrane 34 is further separated from the sinus wall 58. The second predetermined lift distance D2 is typically between 2 and 4 millimeters, and is more typically 3 millimeters. As shown in detail in FIG. 15B, the second lift device typically lifting portion 156 typically has a reduced outer diameter relative the diameter of shaft 154, with a lip 157 formed therebetween. The top surface 159 is placed against the bottom of the freed bridge portion 26a and the freed bridge portion is pushed to the second predetermined lift distance D2, at which point contact between lip 157 and overhang portions 40 prevents further ingress of the second lift device 62. Lifting of the bridge portion 26a and membrane forms a lift region 56 in the gap between the bottom surfaces thereof and the upper surface of the sinus cavity wall 58.

The second lifting device 62 subsequently may be removed, and an elevator material 60 of bone powder and blood plasma may packed into the lift region 56 below lifted sinus membrane 34 and sinus cavity wall 58. Typically the elevator material is made from bone and blood serum obtained from the patient when opening hole 20. The volume of elevator material is typically calculated by making reference to a computer tomography scan of the sinus cavity, and performing volumetric calculations to estimate the size of lift region 56, less the volume to be taken by the implant itself. Alternatively, other suitable method may be used to estimate the amount of elevator material.

Figure 9:
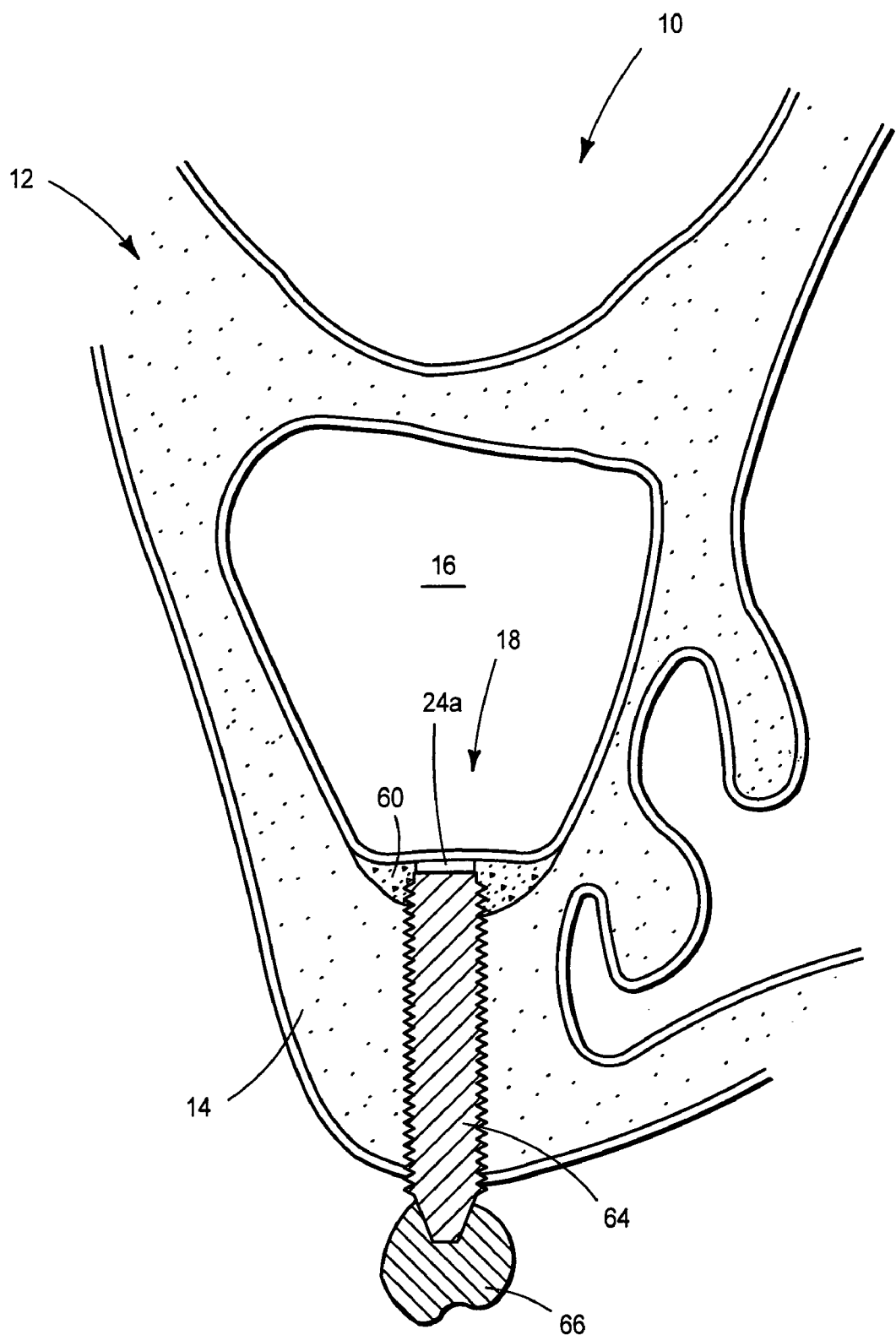
FIG. 9 is a cross-sectional view of an alveolar bone and maxillary sinus cavity, illustrating a dental implant installed according to the implant method illustrated in FIGS. 3–8.

As shown in FIG. 9, after the lift region is packed with elevator material 60, an implant 64 is typically inserted and an artificial tooth 66 is secured to an end thereof. Typically, the diameter of the implant is slightly larger than the hole 20, to form an effective interference fit when inserted. For example, the hole is may be formed to approximately 3 millimeters in diameter, and the implant may have a diameter of 4 millimeters, with an abrasive surface having depressions to a depth of approximately 0.3 millimeters from the outer diameter of the implant 64.

Figure 10:
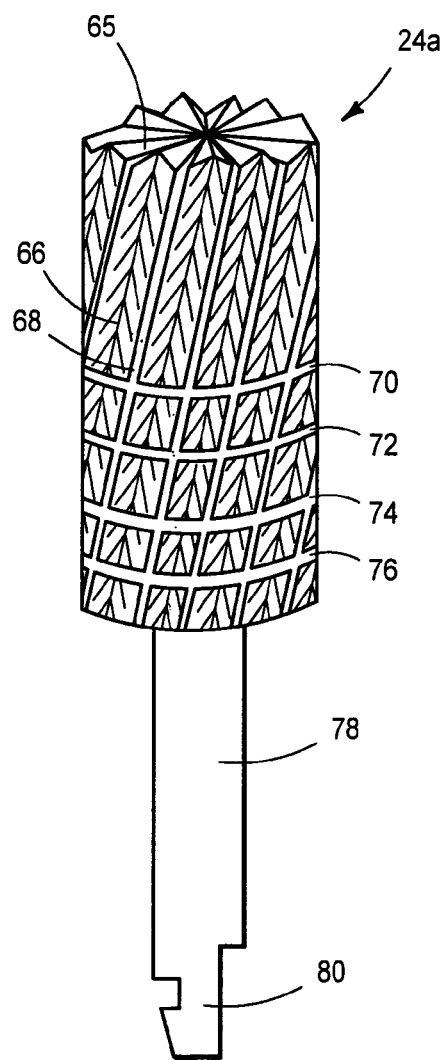
FIG. 10 is a front perspective view of a boring device according to one embodiment of the present invention.

FIGS. 10–16 illustrate a set of devices forming an implant system for performing the above-described implant method. FIG. 10 is a detail view of one embodiment of a boring device 24a according to the present invention. Boring device 24a typically includes a shaft having a top cutting surface 65, a side cutting surface 66, with longitudinal grooves 68 formed at an angle along the along the side cutting surface 66. Longitudinal grooves 68 are configured to allow flow of blood and bone material along the sides of the boring device 24a. Lateral grooves 70–76 serve as markings forming a depth gauge that may be used by a dental surgeon to judge penetration depth of the boring device. The grooves may be calibrated at virtually any suitable distance. For example, groove 70 may formed 4 millimeters from the top cutting surface 65, groove 72 may be formed 6 millimeters from the top cutting surface, groove 74 may be formed 8 millimeters from the top cutting surface, and groove 76 may be formed 10 millimeters from the top cutting surface. A shank 78 with a clip 80 is provided for mounting to a handle for hand rotation, or alternatively to a machine for mechanically driven rotation.

Figure 11:
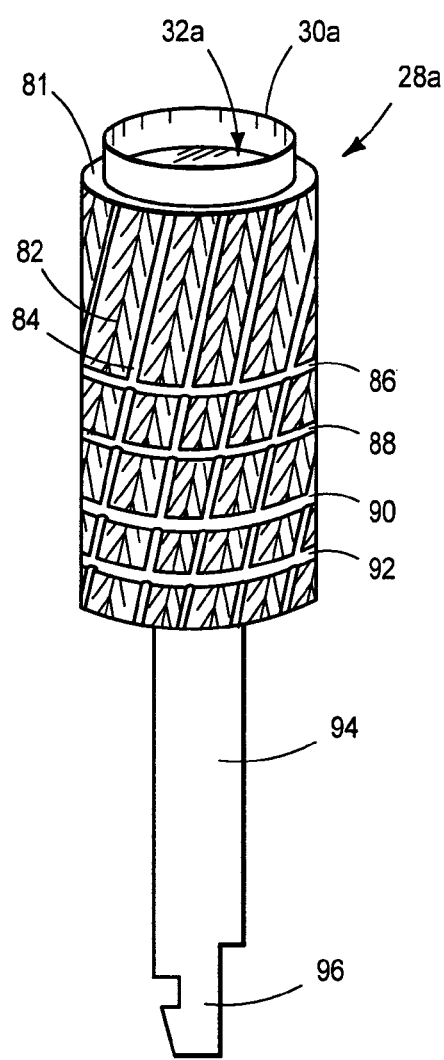
FIG. 11 is a front perspective view of a scoring device according to one embodiment of the present invention.

FIG. 11 illustrates one embodiment of a scoring device 28a according to one embodiment of the present invention. As described above, scoring device 28a typically includes a scoring structure extending upward from a top structure of a shaft of the scoring device. The scoring structure is typically a raised scoring edge extending around the circumference of a cavity 32a. The scoring structure 30a is typically circular and has an outer diameter less than an outer diameter of the shaft of the scoring device, such that a lip 81 is formed intermediate the scoring structure and shaft. Scoring device 28a further includes an exterior cutting surface 82, longitudinal grooves 84, a depth gauge formed by lateral grooves 86–92, a shank 94, and a clip 96. These features are similar to those found in boring device 24a, and will not be redescribed in detail.

Figure 12A:
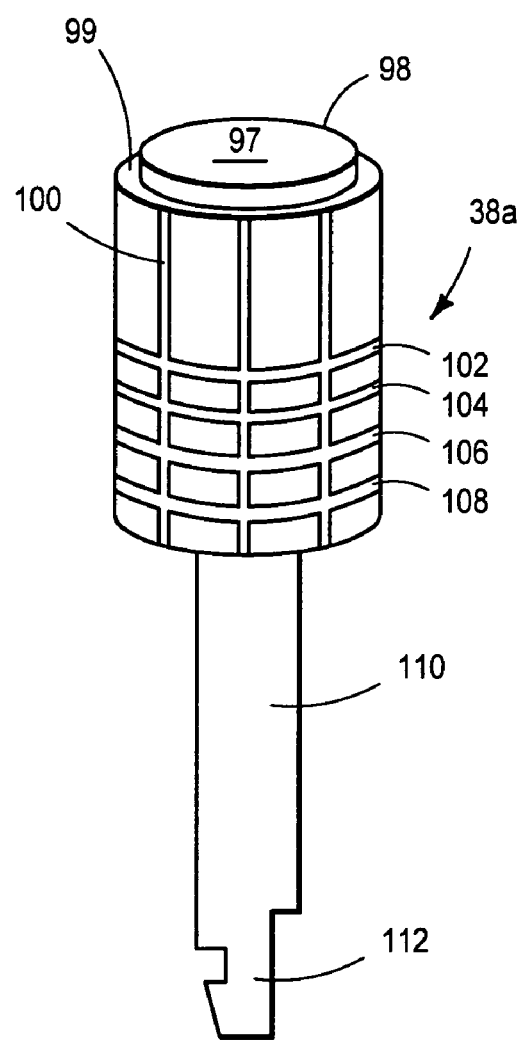
FIG. 12A is a front perspective view of a first lifting device according to one embodiment of the present invention.

FIG. 12A illustrates one embodiment of a first lifting device 38a. First lifting device 38a typically includes a flat top surface 97 positioned on a lifting portion 98. Typically, a lip 99 is formed by a reduction in diameter from a shaft of the first lifting device to the lifting portion 98. The shaft of the first lifting device typically includes longitudinal grooves 100 and lateral grooves 102–108, which form a depth gauge similar to that found on the boring device and scoring device described above. First lifting device 38a further typically includes a shank 110 and clip 112, which may be configured to be attached to a handle or mechanical driver.

Figure 12C:
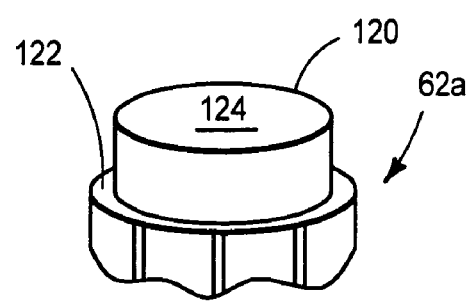
FIG. 12C is a partial front perspective view of a second lifting device according to another embodiment of the present invention.
Figure 12B:
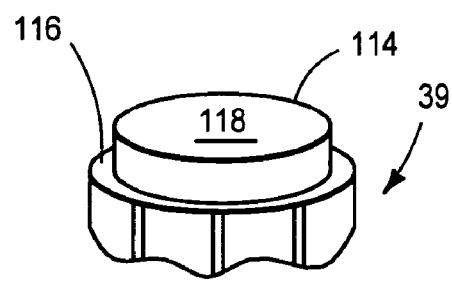
FIG. 12B is a partial front perspective view of an intermediate lifting device according to another embodiment of the present invention.

It will be appreciated that lifting portions of various sizes may be provided on the end of a lifting device of the type shown at 38a. FIG. 12B illustrates an intermediate lifting device 39 with a lifting portion 114 having an intermediate height, as measured between lip 116 and a top surface 118. FIG. 12C shows a second lifting device 62a having lifting portion 120 with a greater height, as measured between lip 122 and top surface 124. According to one embodiment, the height of lifting portion 98 is 1 millimeter, the height of lifting portion 114 is 2 millimeters, and the height of lifting portion 120 is 3 millimeters. While FIGS. 6 and 8 illustrate use of the first and second lifting devices 38, 62, it will be appreciated that an additional intermediate lifting step may be performed using the intermediate lifting device 39, in between the steps illustrated in FIGS. 6 and 8.

Figure 13:
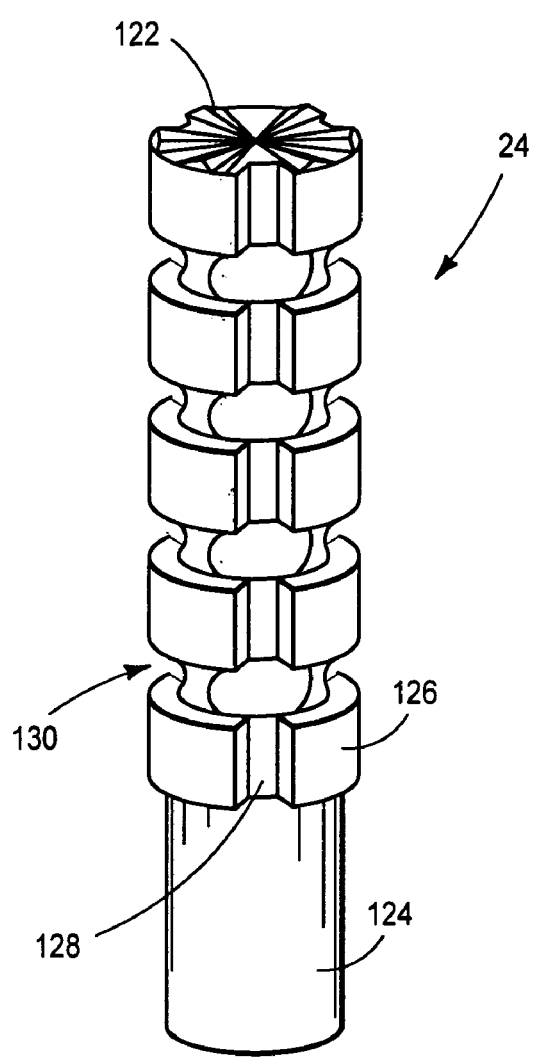
FIG. 13 is a front perspective view of a boring device according to another embodiment of the present invention.

FIG. 13 illustrates a boring device 24 according to another embodiment of the present invention. Boring device 24 includes a top cutting surface 122 positioned at a top of shaft 124. The boring device further includes a plurality of lateral cutting elements 126, which are separated from each other by longitudinal grooves 128, and lateral grooves 130. Typically the boring device and scoring device are of a similar length and width. It will therefore be appreciated that FIG. 13 and 14 are not to scale.

Figure 14:
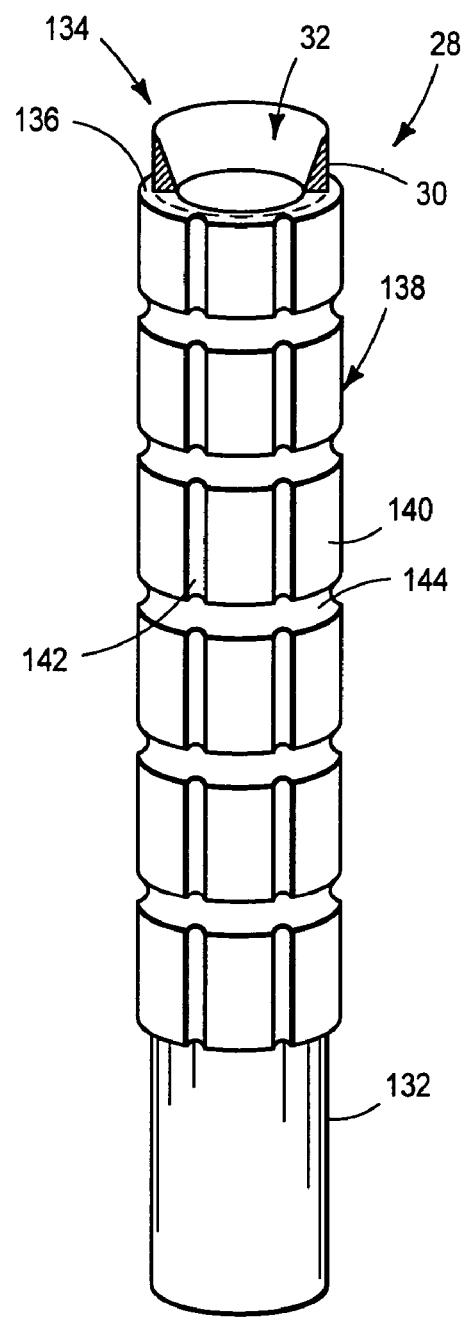
FIG. 14 is a front perspective view of a scoring device according to another embodiment of the present invention.

FIG. 14 illustrates a scoring device 28 according to another embodiment of the present invention. As described in part above, scoring device 28 typically includes a shaft 132 having a raised scoring structure 30 formed at a top end 134 thereof. Raised scoring structure 30 is typically formed around a circumference of cavity 32, which is sized to accommodate bone material when cutting score 36 in bridge portion 26, as described above. The scoring structure 30 is typically circular, and has a diameter that is less than an outer diameter of shaft 132. A lip 136 is formed intermediate scoring structure 30 and shaft 132. Circular bands 138 of raised portions 140 are formed along shaft 132. Raised portions 140 are separated from one another by longitudinal grooves 142, which serve as a depth gauge as described above, and lateral grooves 144, which accommodate the passage of fluid and crushed bone along the length of the shaft.

Figure 15A:
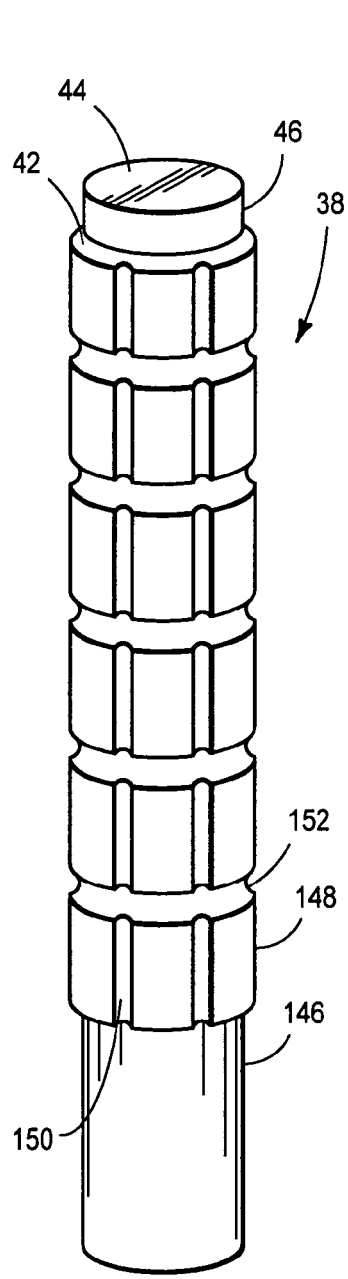
FIG. 15A is a front perspective view of a first lifting device according to another embodiment of the present invention.

FIG. 15A illustrates another embodiment of a first lifting device 38 according to the present invention. First lifting device 38 typically includes a shaft 146 with a lifting portion 46 formed at the top thereof, and a lip 42 formed therebetween. A top surface 44 of the lifting portion is typically flat and spaced apart from lip 42. The height of the lifting portion 46 is sized so that when inserted into the hole 20, the bridge portion 26 is raised to the first predetermined lift distance D1, as shown in FIG. 6. The outer diameter of the lifting portion 46 is typically less than the outer diameter of shaft 146. Shaft 146 further includes a plurality of raised portions 148 separated by longitudinal grooves 150 and lateral grooves 152, similar to scoring device 28.

Figure 15B:
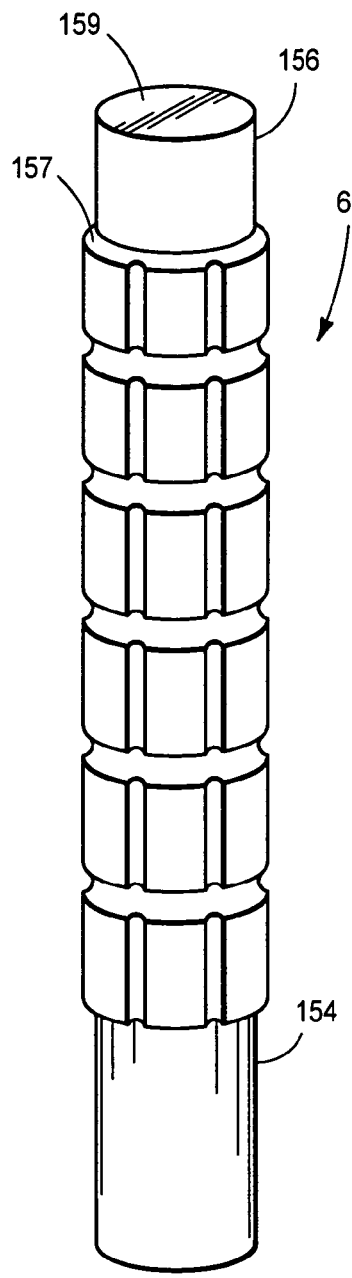
FIG. 15B is a front perspective view of a second lifting device according to another embodiment of the present invention.

FIG. 15B illustrates another embodiment of a second lifting device 62, having a shaft 154 and lifting portion 156 positioned at a top end thereof. Lip 157 is positioned intermediate the shaft and lifting portion. A flat top surface 159 is typically provided at a height relative to lip 157 sized such that the lifting portion raises the bridge portion to the second predetermined lift distance D2, when inserted into hole 20 as shown in FIG. 8.

FIG. 16A illustrates a membrane separation elevator 48 having a shaft 158, with indicia or grooves 160–166 positioned along a length thereof to provide a depth gauge. As shown in FIG. 16B, membrane separation elevator 48 includes a substantially flat, generally triangular head, formed with large diameter radiuses, so as to minimize sharp corners that may damage sinus membrane 34. It will be appreciated that other suitable shapes may be used for head 168, such as circular or oval shapes.

Figure 17:
FIG. 17 is a pre-operative intra-oral photograph of a dental implant patient.
Figure 18:
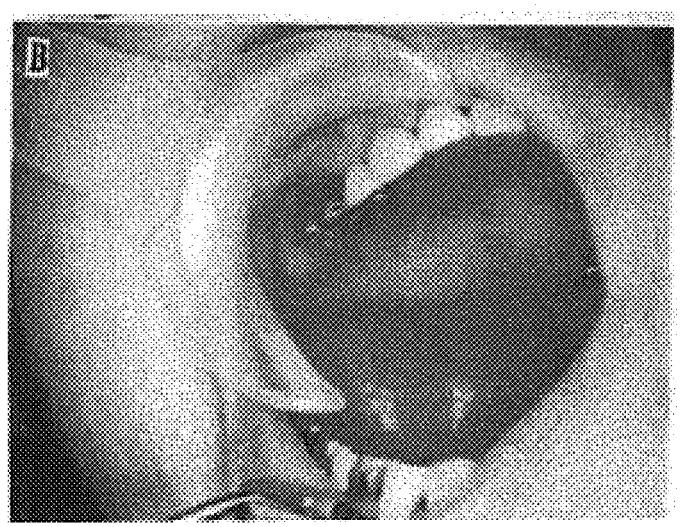
FIG. 18 is a post-operative intra-oral photograph of the patient of FIG. 17, showing an installed implant.

FIGS. 17 and 18 are pre-operative and post-operative intra-oral photographs of a patient on whom the above-described devices and methods were used to install a dental implant.

Figure 19:
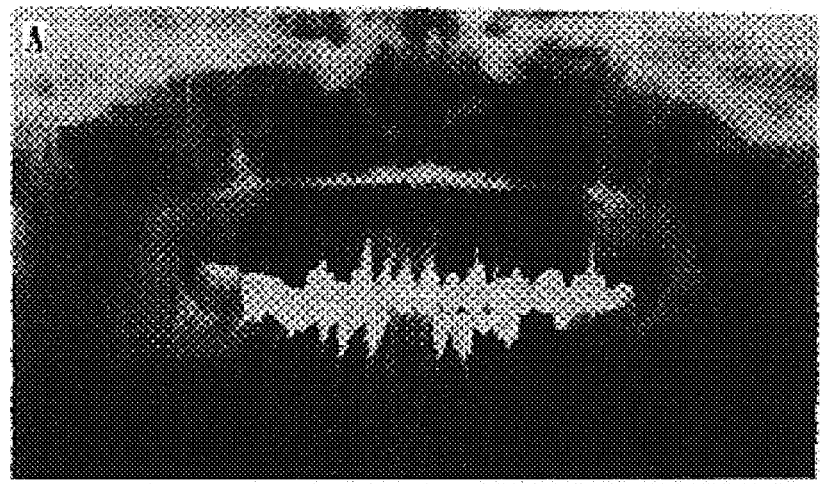
FIG. 19 is a pre-operative panoramic tomography of the patient of FIG. 17.
Figure 20:
FIG. 20 is a post-operative panoramic tomography of the patient of FIG. 17, showing an installed implant.

FIGS. 19 and 20 are pre-operative and post-operative panoramic tomographies of the patient of FIGS. 17 and 18.

Figure 21:
FIG. 21 is a pre-operative inter-oral radiography of an implant region of the patient of FIG. 17.
Figure 22:
FIG. 22 is a post-operative inter-oral radiography of an implant region of the patient of FIGS. 17, showing an installed implant.

FIGS. 21 and 22 are pre-operative and post-operative inter-oral radiographies of an implant region of the patient of FIGS. 17 and 18.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

The invention claimed is:

1. A dental implant method, comprising:

forming a hole in an alveolar bone of a maxilla, adjacent a sinus cavity having a sinus membrane lining the sinus cavity, the hole being fanned so as to leave a bridge portion separating the hole from a bottom surface of a sinus cavity wall;

separating the bridge portion from the sinus cavity wall to form an overhang portion along a side of the hole, adjacent an upper opening of the hole; and lifting the bridge portion and the sinus membrane together at least partially into the sinus cavity, to raise the bridge portion a first predetermined lift distance into the sinus cavity;

wherein the step of lifting the first predetermined lift distance is performed by a first lifting device that includes a shaft having a lip and a lifting portion of a first height;

wherein the lip is step-shaped and the overhang portion is formed to be complementarily step-shaped; and wherein as the first lifting device is inserted into the hole, ingress of the first lifting device is stopped by contact between the step-shaped overhang portion of the hole and the step-shaped lip of the first lifting device, to thereby position the bridge portion at the first predetermined lift distance into the sinus cavity.

2. The dental implant method of claim 1, wherein lifting is accomplished without separating the bridge portion from the sinus membrane.

3. The dental implant method of claim 1, further comprising separating the sinus membrane from the sinus cavity wall, to thereby create a gap.

4. The dental implant method of claim 3, further comprising placing elevator material into the gap.

5. The dental implant method of claim 4, wherein the elevator material includes crushed bone and blood serum.

6. The dental implant method of claim 5, further comprising inserting a dental implant into the hole, such that an inward end of the implant extends into the gap filled by the elevator material, and is surrounded by the elevator material.

7. The method of claim 6, wherein the elevator material is configured to harden over time to increase the effective thickness of the maxilla, thereby providing stability for the implant.

8. The method of claim 3, wherein the step of separating the sinus membrane from the sinus cavity wall is performed by a separator elevator having a flat head, by rotating the separator elevator around a circumference of an upper opening of the hole.

9. The method of claim 8, further comprising determining the depth of the separator elevator into the hole by referencing a depth gauge formed on a handle of the separator elevator.

10. The dental implant method of claim 1, wherein the step of lifting raises the bridge portion a first predetermined lift distance into the sinus cavity, the method further comprising:

separating the sinus membrane from the sinus cavity wall; and further lifting the bridge portion a second predetermined lift distance within the sinus cavity.

11. The dental implant method of claim 10, wherein the step of lifting to the second predetermined height is performed by a second lifting device that includes a shaft having a lip and a lifting portion of a second height higher than the first height, wherein as the second lilting device is inserted into the hole, ingress of the second lifting device is stopped by contact between the overhang portion of the hole and the lip of the second lifting device, to thereby position the bridge portion at the second predetermined lift distance into the sinus cavity.

12. The method of claim 11, wherein the lifting portion of the second lifting device includes a substantially flat top surface configured to contact and lift the bridge portion.

13. The dental implant method of claim 10, wherein the first predetermined lift distance is between about 0.5 and 1.5 millimeters.

14. The dental implant method of claim 10, wherein the first predetermined lift distance is about 1 millimeter.

15. The dental implant method of claim 10, wherein the second predetermined lift distance is between about 2 and 4 millimeters.

16. The dental implant method of claim 10, wherein the second predetermined lift distance is about 3 millimeters.

17. The dental implant method of claim 10, wherein the bridge portion has a thickness of between about 0.5 and 2 millimeters.

18. The dental implant method of claim 10, wherein the bridge portion has a thickness of about 1 millimeter.

19. The method of claim 1, wherein the lifting portion of the first lifting device includes a substantially flat top surface configured to contact and lift the bridge portion.

20. A dental implant method, comprising:

drilling a hole in maxillary alveolar bone;

forming a bridge portion intermediate the hole and a lower surface of a sinus cavity;

scoring the bridge portion, so as to create a score inward of a wall of the hole;

lifting the bridge portion a predetermined distance into the sinus cavity to thereby detach the bridge portion from the bone along the score, to raise a sinus membrane of the sinus cavity together at least partially into the sinus cavity, and to form an overhang portion along a side of the hole outward of the score;

separating the sinus membrane from a wall of the sinus cavity, to thereby create a gap therebetween;

placing elevator material into the gap; and inserting an implant into the hole, such tat an inward end of the implant extends into the gap with the elevator material placed therein, and is surrounded by the elevator material;

wherein the step of lifting the bridge portion a predetermined distance is performed by a lifting device that includes a shaft having a lip and a lifting portion of a first height;

wherein the lip is step-shaped and the overhang portion is formed to be complementarily step-shaped; and wherein ingress of the lifting device is stopped by contact between the step-shaped overhang portion of the hole and the step-shaped lip of the lifting device, to thereby position the bridge portion at the predetermined lift distance into the sinus cavity.

21. A dental implant method, comprising:

forming a hole in an alveolar bone of a maxilla, adjacent a sinus cavity having a sinus membrane lining the sinus cavity, the hole being formed so as to leave a bridge portion separating the hole from a bottom surface of a sinus cavity wall;

separating the bridge portion from the sinus cavity wall to form an overhang portion along a side of the hole; and lifting the bridge portion and the sinus membrane together at least partially into the sinus cavity, to raise the bridge portion a first predetermined lift distance into the sinus cavity;

separating the sinus membrane from the sinus cavity wall; and further lifting the bridge portion a second predetermined lift distance within the sinus cavity;

wherein the step of lifting the first predetermined lift distance is performed by a first lifting device tat includes a shaft having a lip and a lifting portion of a first height;

wherein the step of lifting to the second predetermined height is performed by a second lifting device that includes a shaft having a lip and a lifting portion of a second height higher than the first height;

wherein as the first lifting device is inserted into the hole, ingress of the first lifting device is stopped by contact between the overhang portion of the hole and the lip of the first lifting device, to thereby position the bridge portion at the first predetermined lift distance into the sinus cavity; and wherein is the second lifting device is inserted into the hole, ingress of the second lifting device is stopped by contact between the overhang portion of the hole and the lip of the second lifting device, to thereby position the bridge portion at the second predetermined lift distance into the sinus cavity.

* * * * *

UNITED STATES PATENT AND TRADEMARK OFFICE
CERTIFICATE OF CORRECTION

PATENT NO. : 7,125,253 B2
APPLICATION NO. : 10/956559
DATED : October 24, 2006
INVENTOR(S) : Akira Kitamura and Ryoji Kitamura It is certified that error appears in the above-identified patent and that said Letters Patent is hereby corrected as shown below:

In Column 2, line 55, insert --be-- between "to" and "inserted".

In Column 4, line 50, delete "26" and insert --24-- therefor.

In Column 5, line 12, delete both instances of "26" and insert in both locations --36-- therefor.

In Column 5, line 46, delete "relay" and insert --rely-- therefor.

In Column 5, line 66, delete "162" and insert --160-- therefor.

In Column 6, line 39, delete "66" and insert --64a-- therefor.

In Column 6, line 42, delete "is" between "hole" and "may".

In Column 6, line 53, delete "the along" between "along" and "the side".

In Column 10, line 30, delete "tat" and insert --that-- therefor.

In Column 10, line 63, delete "tat" and insert --that-- therefor.

In Figure 9, delete "66" and insert --64a-- therefor.

Signed and Sealed this

Third Day of April, 2007

JON W. DUDAS
*Director of the United States Patent and Trademark Office*